(12) United States Patent
Price et al.

(10) Patent No.: US 6,410,722 B1
(45) Date of Patent: Jun. 25, 2002

(54) HUMAN AND MAMMALIAN DATA REPLICATION ORIGIN CONSENSUS SEQUENCES

(75) Inventors: Gerald B. Price, Montreal; Maria Zannis-Hadjopoulos, Westmount; Torsten O. Nielsen, British Columbia; Nandini H. Cossons, Kingston, all of (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/328,750

(22) Filed: Jun. 9, 1999

Related U.S. Application Data

(63) Continuation of application No. PCT/CA97/00972, filed on Dec. 12, 1997.
(60) Provisional application No. 60/047,322, filed on May 21, 1997, and provisional application No. 60/033,374, filed on Dec. 16, 1996.

(51) Int. Cl.$^7$ ................................................ C07H 21/04
(52) U.S. Cl. ....................................................... 536/24.1
(58) Field of Search ......................................... 536/24.1

(56) References Cited

FOREIGN PATENT DOCUMENTS

WO      WO 92 07080      4/1992

OTHER PUBLICATIONS

Landry S. et al., *Biochimica et Biophysica Acta*, vol. 1088, No. 1, pp. 234–244, 1991.
Rao B.S. et al; *Embl. Nucleotide/Protein Database*, vol. 87, pp. 233–242, 1990.
Todd A. et al., *Journal of Cellular Biochemistry*, vol. 57, No. 2, pp. 280–289, 1995.
Wu C. et al., *Biochimica et Biophysica Acta*, vol. 1174, No. 3, pp. 241–257, 1993.
Calos, M.P., *Trends in Genetics*, vol. 12, No. 11, pp. 463–466, 1996.
Cossons N., et al., Journal of Cellular Biochemistry, vol. 67, No. 4, pp. 439–450, 1997.

*Primary Examiner*—Terry McKelvey
(74) *Attorney, Agent, or Firm*—Nixon Peabody LLP

(57) ABSTRACT

The present invention relates to a human or mammalian DNA replication origin consensus sequence which consists of a sequence selected from the group consisting of CCTMDAWKSGBYTSMAAWYWBCMYTTRSCAAATTCC (SEQ ID NO:1); and AWMTWAAKRAWRWWKKDAVW-WGAKRWWKWVWHRASSACMDWKAAK-TWKGGWTWARRYWKGRKMWWTWKAWS-DATAKWWWKDAKWKMWRKTT (SEQ ID NO:4). A method for the control of initiation of mammalian DNA replication which comprises the steps of: a) inserting a consensus sequence coding for a sequence of the present invention together with a DNA fragment to form a vector capable of expression of the DNA fragment; b) introducing the vector of step a) into mammalian cells in vitro.

2 Claims, 9 Drawing Sheets

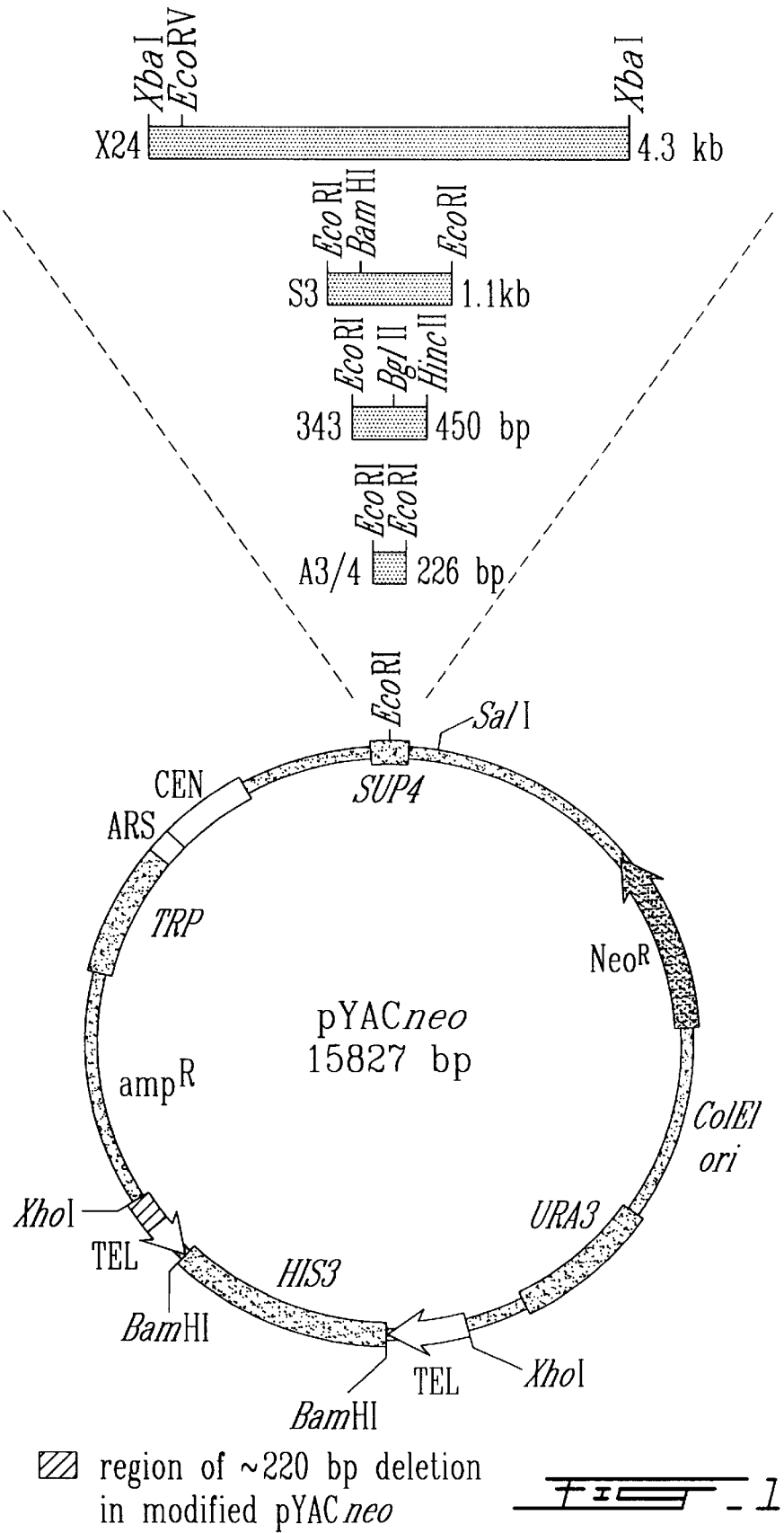

Y.343 clone 2

Y.A3/4 clone 9

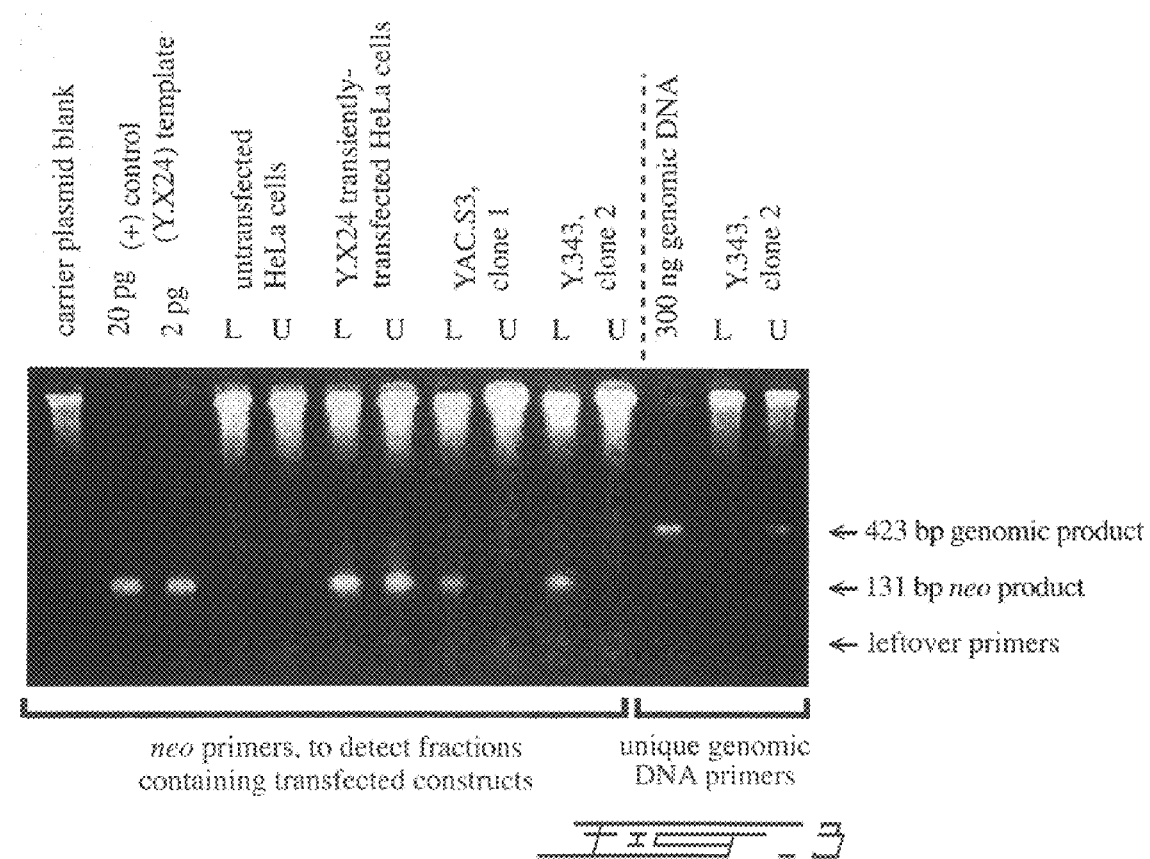

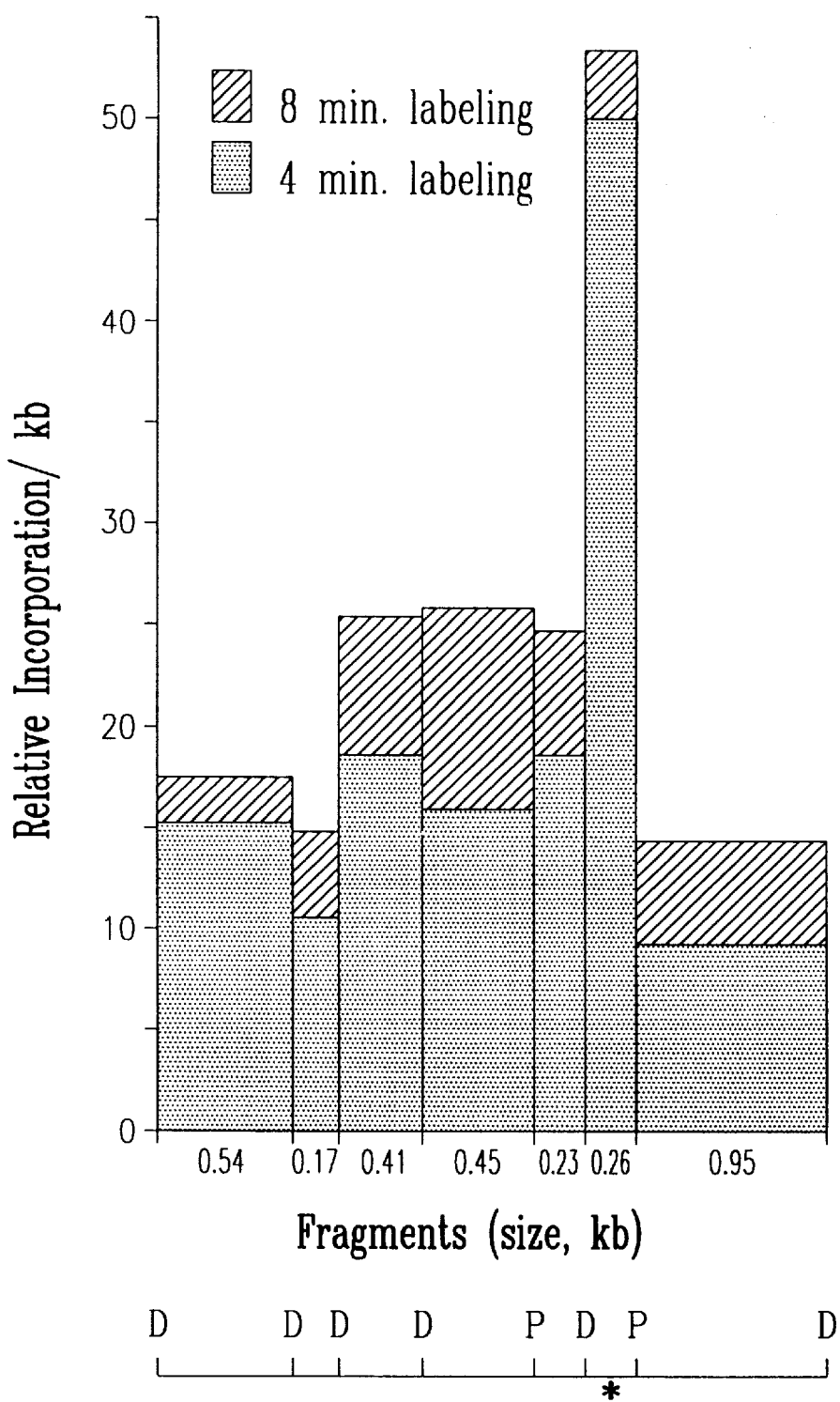
*denotes position of 'alphaconsensus' A3/4
The rest of the DNA is pCRscript vector sequence.
DdeI(D)/ PvuII(P) digest

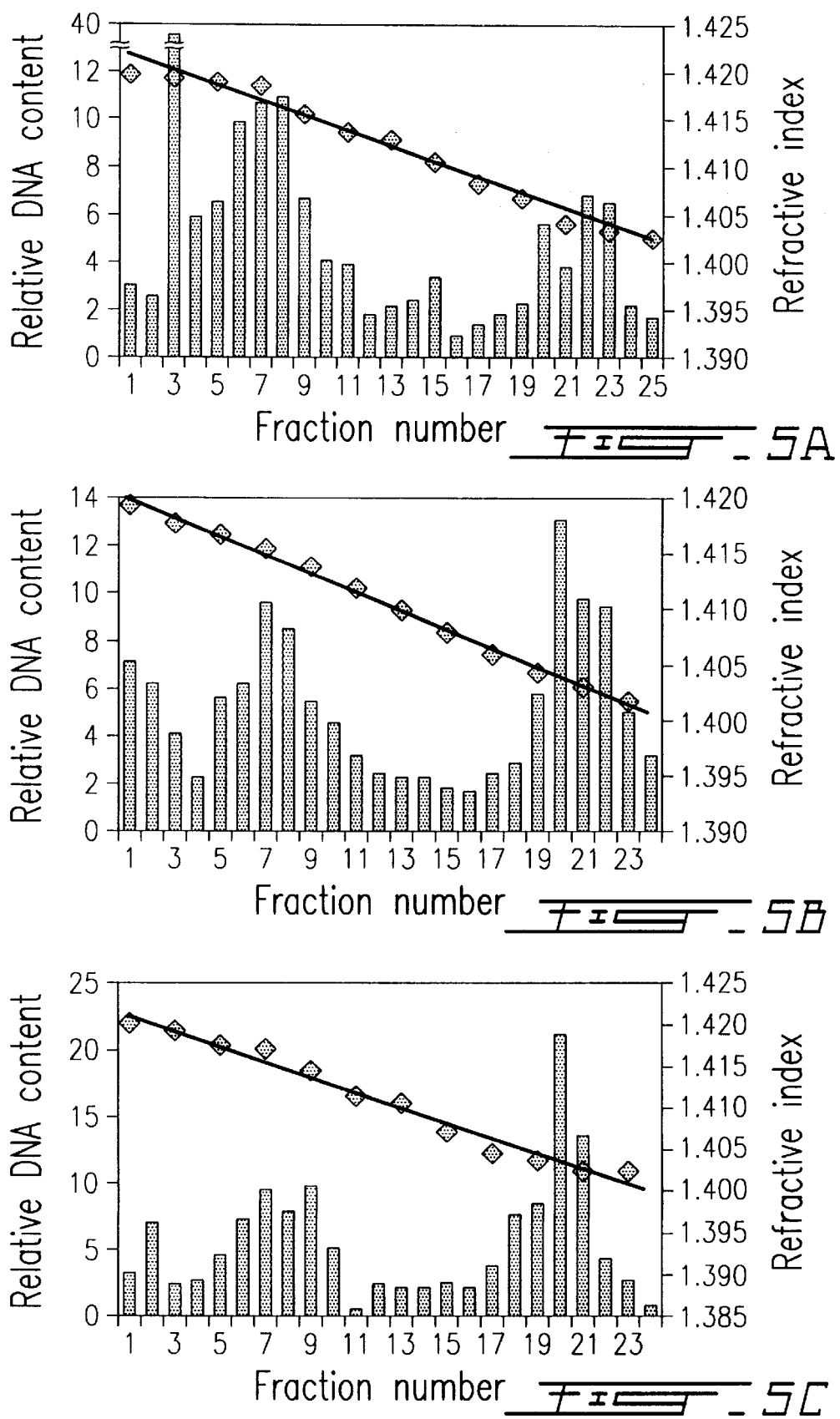

```
                              SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: Genomic DNA (xi) SEQUENCE DESCRIPTION: SEQ ID NO: 1:

CCTMDAWKSG BYTSMAAWYW BCMYTTRSCA AATTCC                              36

(2) INFORMATION FOR SEQ ID NO: 2:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: Genomic DNA (xi) SEQUENCE DESCRIPTION: SEQ ID NO: 2:

CCTCAAAGCG CTTGAAAATC TCCACTTGCA AATTCC                              36

(2) INFORMATION FOR SEQ ID NO: 3:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: Genomic DNA (xi) SEQUENCE DESCRIPTION: SEQ ID NO: 3:

DAWKSGBYTS MAAWYWBCMY TTRSCAAATT                                     30

(2) INFORMATION FOR SEQ ID NO: 4:

(i) SEQUENCE CHARACTERISTICS:
              (A) LENGTH: 30 base pairs
              (B) TYPE: nucleic acid
```

(C) STRANDEDNESS: single
        (D) TOPOLOGY: linear (ii) MOLECULE TYPE: Genomic DNA (xi) SEQUENCE DESCRIPTION: SEQ ID NO: 4:

TATGTGTTTT CATATTTTGT TTGGCATATT                                30

(2) INFORMATION FOR SEQ ID NO: 5:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 5:

AWMTWAAKRA WRWWKKDAVW WGAKRWWKWV WHRASSACMD WKAAKTWKGG WTWARRYWKG   60

RKMWWTWKAW SDATAKWWWK DAKWKMWRKT T                                 91

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 6:

TCAGGACATA GCGTTGGCT                                            19

(2) INFORMATION FOR SEQ ID NO: 7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 7:

CGTCAAGAAG GCGATAGAA                                            19

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 8:

TGTGTATGGG ACGGTAGTCA                                           20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 9:

GGAGCAAGGC AGAACTACTC                                                        20

(2) INFORMATION FOR SEQ ID NO: 10:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 10:

CCTCAAATGG TCTCCAATTT TCCTTTGGCA AATTCC                                      36

(2) INFORMATION FOR SEQ ID NO: 11:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 11:

CCTCGATGGG TTTGCAAATT CCCCTTAGCA AATTCC                                      36

(2) INFORMATION FOR SEQ ID NO: 12:

(i) SEQUENCE CHARACTERISTICS:
            (A) LENGTH: 91 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 12:

ATATAAATGA TAAAGTAAAA TGAGGATTAA ATAAGGACCT TTAATTAGGG TTTAGATAGG            60

GGATTTATAA CGATATTATT TATAGCAGTT T                                           91

(2) INFORMATION FOR SEQ ID NO: 13:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 13:

TTCCGAATAC CGCAAG                                                            16

(2) INFORMATION FOR SEQ ID NO: 14:

(i) SEQUENCE CHARACTERISTICS:
            (A) LENGTH: 193 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 14:

```
AATTCCTGCA GCCCGGGGGA TCCGCCCATT AACCCTCACT AAAGGGAACA AAAGCTGGGT      60

ACCTGAGCTC CAATTCACTG GCCGTCGTTT TACGGGCTAG AGCGGCCGCC ACCGCGGTGG     120

AGCTCCAGCT TTTGTTCCCT TTAGTGAGGG TTAATTGCGC GCTTGGCGTA ATCATGGTCA     180

TAGCTGTTTC CGG                                                        193
```

(2) INFORMATION FOR SEQ ID NO: 15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 15:

```
CCTCTAATGG CTTCCAAACA TCACTTGGCA AATTCC                               036
```

HUMAN AND MAMMALIAN DATA REPLICATION ORIGIN CONSENSUS SEQUENCES

This application is a continuation application of International Application PCT/CA97/00972 filed on Dec. 12, 1997, which designated the United States and which is now abandoned, and which claims the benefit of priority of U.S. Provisional Application No. 60/047,322, filed May 21, 1997 and U.S. Provisional Application No. 60/033,374 filed Dec. 16, 1996.

BACKGROUND OF THE INVENTION (a) Field of the Invention

The invention relates to human and mammalian DNA replication origin consensus sequences; the use of consensus sequences for control of initiation of mammalian DNA replication; small sequences which will allow the maintenance of circular plasmid constructs which are capable of being replicated semiconservatively in proliferating mammalian cells; to small sequences suitable for use in human gene therapy; to small sequences suitable for inclusion in mammalian and human artificial chromosome vectors; to a protein binding to double-stranded DNA; to an anti-gene to DNA replication; and to a method of inhibiting DNA replication in vitro or in vivo.

(b) Description of Prior Art

Building a human artificial chromosome would not only provide a valuable tool for addressing difficult questions about chromosome biology, but would also create an all-human transfection vector with the capacity to carry large chromosomal regions including complete transcriptional units, from even the largest genes, for the purpose of complementation mapping, or for gene therapy (Huxley, C. (1994) Gene Ther. 1:7–12).

Artificial chromosomes require three cis-acting functional components: replication origins, telomeres, and a centromere. S. cerevisiae origin-containing yeast ARS (autonomously replicating sequence) plasmids provided the basis for the addition of telomeres, TEL, and centromere, CEN elements to complete the construction of stable yeast artificial chromosomes, or YACs (Murray, A. W. & Szostak J. W. (1983) Nature, 305, 189–193). A similar strategy proved successful for artificial chromosome assembly in the fission yeast Schizosaccharomyces pombe, in spite of the far more complicated structure of its centromeres (Hahnenberger, K. M. et al. (1989) Proc. Nat. Acad. Sci. USA, 86:577–581).

The first component required in such a "ground up" strategy for the assembly of a prototype human artificial chromosome is a functional human replication origin. Different techniques have permitted the identification of a limited but rapidly-increasing number of putative and proven mammalian origins of DNA replication (DePamphilis, M. L. (1993) Annu. Rev. Biochem. 62:29–63).

Our group has been able to isolate large numbers of putative origins using such techniques as nascent strand extrusion (Kaufmann, G. et al. (1985) Mol. Cell. Biol., 5:721–727) and anti-cruciform immunoaffinity purification (Bell, D. et al. (1991) Biochim. Biophys. Acta, 1089:299–308); these sequences permit short-term autonomous replication of plasmids transfected into human cells, and can act as replication origins in their native chromosomal position (Wu, C. et al. (1993a) Biochim. Biophys. Acta, 1174:241–257).

To use such isolated origin sequences for the construction of a first stage human artificial chromosome, they must be cloned into a circular vector which permits transfection into human cells and selection of transfected clonal subpopulations, and has the capacity for further modification to carry human-functional telomeres and putative centromere elements which could be hundreds of kilobases. In addition, methods are adapted and applied which demonstrate that these constructs are maintained in long-term culture as independent episomal elements, not integrated into a host chromosome.

We have identified CDNA clones which contain ARS (Wu, C. et al. (1993a) Biochim. Biophys. Acta, 5 1174:241–257) and demonstrated that clone 343, located on chromosome 6q (Shihab-El-Deen, A. et al. (1993) Somat. Cell Mol. Genet. 19:103–109), can be mapped as a chromosomal origin in vivo (Wu, C. et al. (1993b) Biochim. Biophys. Acta, 1174:258–266). We have also demonstrated that the bi-directional origin (oriβ) of the dihydrofolate reductase, DHFR, locus from Chinese hamster), within small or large fragments, has ARS activity in vivo in DpnI resistance assays after transfection into HeLa cells, and in vitro with our mammalian in vitro DNA replication system (Zannis-Hadjopoulos, M. et al. (1994) Gene, 151:273–277). (We also showed that the in vivo and in vitro replication assays of ARS and origin function give the same results, and initiation of replication in the plasmid constructs occurs within the oriβ containing insert).

We have also conducted the identification and characterization of an ors (origin enriched sequence) binding activity (now also referred to as origin binding activity) (OBA) partially purified from HeLa cell extracts that are used in our in vitro DNA replication system, co-purifying with known replication proteins (Ruiz, M. T. et al. (1995) J. Cell. Biochem. 58:221–236). The regulation of eukaryotic DNA replication is one of the most important biologic mechanisms. We have demonstrated the long-term maintenance as episomes of origin containing fragments (S3 (Nielsen, T. et al. (1994) Mol. Gen. Genet. 242:280–288) and 343) under selection in a YACneo plasmid, further demonstrating the functionality of small fragments containing ARS as origins.

Although previous sequence analysis failed to reveal specific nucleotide consensus sequences, we have now had the opportunity to examine larger numbers of monkey and human ARS and to group small DNA fragments containing ARS activity in order to derive two putative minimal core ARS consensus sequences (36 bp and 91 bp). Preliminary analysis by in vivo and in vitro replication assays indicates that both are capable of functioning as origins in these assays of episomal replication in mammalian cells. Furthermore, one specific sequence has been shown to bind to OBA and to be as effective of a competitor for binding as the fragments of the 186 bp minimal ARS of the ORS8 origin (Todd, A. et al. (1995) J. Cell. Biochem. 58:221–236).

Because of the collective weight of our original work and resources, we are confident in the likelihood of identification of a mammalian minimal core ARS consensus sequence, which like the identification of the yeast minimal core ARS consensus should rapidly advance discoveries of the mechanism of DNA replication in mammalian cells.

It would be highly desirable to be provided with a minimal consensus sequence from which versions of human core ARS could be used to create shuttle vector constructs for use in definition of essential mammalian chromosomal elements that are required for the maintenance of chromosome function, and for use in gene therapy.

SUMMARY OF THE INVENTION

One aim of the present invention is to provide consensus sequences for control of initiation of mammalian DNA replication.

Another aim of the present invention is to provide small sequences which will allow the maintenance of circular plasmid constructs which are capable of being replicated semiconservatively in proliferating mammalian cells.

Another aim of the present invention is to provide small sequences suitable for inclusion in mammalian and human artificial chromosome vectors.

In accordance with one embodiment of the present invention there is provided a specific 36-bp consensus sequence called 'alphaconsensus' and a specific 91-bp consensus sequence called 'uniorsconsensus'.

In accordance with another embodiment of the present invention the alphaconsensus comprises the nucleotide sequence set forth as follows:

CCTMDAWKSGBYTSMAAWYWBCMYTTRSCA
       AATTCC                                (SEQ ID NO:1).

The alphaconsensus sequence (36 bp) was derived from autonomously replicating sequences associated with alpha-satellite sequences from African Green Monkey CV-1 cells (ORS14 & ORS23 Landry, S. & Zannis-Hadjopoulos, M. (1991) *Biochim. Biophys. Acta*, 1088:234–244) and associated with alpha-satellite sequences from normal human skin fibroblasts (F5 and F20 Nielsen, T. et al. (1994) *Mol. Gen. Genet.* 242:280–288).

The alphaconsensus is able to replicate DNA in BVDR incorporation assay using murine fibroblasts NIH 3T3 and murine embryonic carcinomas cells P19.

In accordance with another embodiment of the present invention the consensus is a functional variant thereof having a sequence with at least 70% homology with the alphaconsensus, such as Y.343 which is a natural occurring variant version of the alphaconsensus or a functional fragment thereof of at least 20 nucleotides which includes modifications and gap insertions of one to five nucleotides.

Such variants which exhibit a 70% homology with the alphaconsensus include, without limitation, the following sequences with their respective homology being illustrated:

In accordance with the present invention there is provided a method for the control of initiation of mammalian DNA replication which comprises the steps of:
    a) inserting a consensus sequence coding for a sequence of the present invention together with a DNA fragment to form a vector capable of expression of the DNA fragment;
    b) introducing the vector of step a) into mammalian cells in vitro.

In step b), the vector is introduced by a standard method selected from the group consisting of calcium phosphate co-precipitation transfection, electroporation, microinjection, and liposome-mediated transfection.

In accordance with the present invention there is provided a DNA sequence for the maintenance of circular plasmid constructs which are capable of being replicated semiconservatively in proliferating mammalian cells, which comprises at least one consensus sequence consisting of a sequence of the present invention.

In accordance with the present invention there is provided a DNA sequence suitable for inclusion in mammalian and human artificial chromosome vectors, which comprises at least one consensus sequence consisting of a sequence of the present invention.

In accordance with the present invention there is provided a protein derived from LHeLa cell extracts which binds to double-stranded DNA, which is of about 150 kDa in a glycerol gradient and which consists in 2 subunits of approximately 86 and 70 kDa respectively.

In accordance with the present invention there is provided an anti-gene to DNA replication, which comprises a doubled-stranded form of a consensus sequence of the present invention.

In accordance with the present invention there is provided a method of inhibiting DNA replication in vitro or in vivo, which comprises administering a consensus sequence of the present invention in single-stranded or double-stranded form.

|   |   | I? |   |
|---|---|---|---|
| 1 | CCTMDAWKSGBYTSMAAWYWBCMYTTRSCAAATTCC | 36 | (SEQ ID NO:1) |
| 97 | CCTCAAAGCGCTTGAAAATCTCCACTTGCAAATTCC | 132 | (SEQ ID NO:2) |
| 5 | DAWKSGBYTSMAAWYWBCMYTTRSCAAATT | 34 | (SEQ ID NO:3) |
| 78 | TATGTGTTTTCATATTTTGTTTGGCATATT | 107 | (SEQ ID NO:4). |

In accordance with the present invention the uniorsconsensus comprises the nucleotide sequence set forth as follows:

AWMTWAAKRAWRWWKKDAVWWGAKRWWK-
       WVWHRASSACMDWKAAKTWKGGWTWAR-
       RYWKGRKMWWTWKAWSDATAKWWWKDAK-
       WKMWRKTT                           (SEQ ID NO:5).

The uniorsconsensus sequences (91 bp) was derived from autonomously replicating sequences of low copy or unique sequence from African Green Monkey CV-1 cells which include ORS8 (GenBank Accession M26221) (Kaufmann, G. et al. (1985) Mol. Cell. Biol., 5:721–727; Frappier, L. & Zannis-Hadjopoulos, M. (1987) *Proc. Nati. Acad. Sci. USA*, 84:6668–6672), and ORS13, ORS20, ORS24, and ORS25, (Landry, S. & Zannis-Hadjopoulos, M. (1991) *Biochim. Biophys. Acta*, 1088:234–244).

In accordance with another embodiment of the present invention the consensus is a functional variant thereof having a sequence with at least 70% homology with the uniorsconsensus.

The abbreviations used herein for designating the nucleotides are as follows:

| Code | Group | Nucleotide(s) |
|---|---|---|
| A | A | adenine |
| C | C | cytosine |
| G | G | guanine |
| T | T | thymine (in DNA) |
| U | U | uracil (in RNA) |
| Y | C or T(U) | pyrimidine |
| R | A or G | purine |
| M | A or C | amino |
| K | G or T(U) | keto |
| S | G or C | strong interaction (3 hydrogen bonds) |
| W | A or T(U) | weak interaction (2 hydrogen bonds) |
| H | A or C or T(U) | not-G |
| B | G or T(U) or C | not-A |
| V | G or C or A | not-T or not-U |

-continued

| Code | Group | Nucleotide(s) |
|---|---|---|
| D | G or A or T(U) | not-C |
| N | G,A,C or T(U) | any |

BRIEF DESCRIPTION OF THE DRAWINGS

FIG. 1 is a diagram of pYACneo vectors and cloned mammalian orgin and consensus sequences;

FIG. 3 illustrates PCR analysis of supercoiled episomal and linear genomic DNA fractions;

FIG. 4 illustrates mammalian in vitro DNA replication of a plasmid containing one version of the 36-bp consensus sequence, A3/4, with initiation of DNA replication occurring within the region containing the consensus sequence;

FIGS. 5A–5C illustrate bromodeoxyuridine in vivo labeling of individual aiphaconsensus plasmid clones;

Figure 2A:
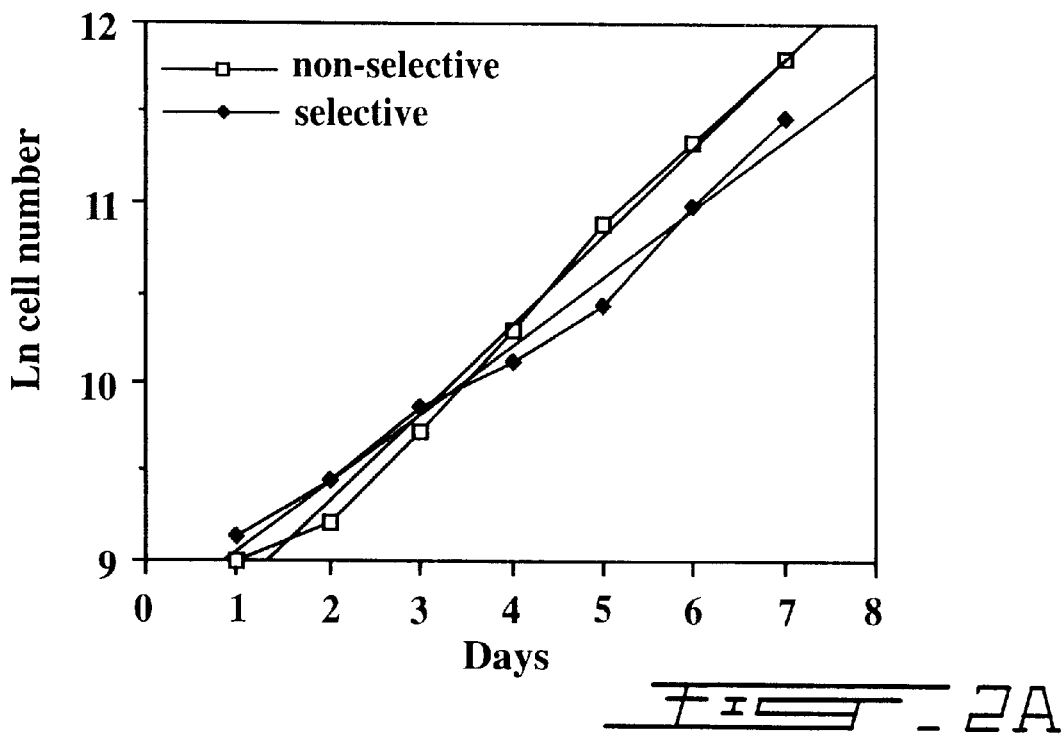
FIGS. 2A–2B illustrate growth curves of two representative HeLa clonal subpopulations, derived from transfections with mammalian origin-containing, modified pYACneo and pYACneo vectors.

DETAILED DESCRIPTION OF THE INVENTION pYACneo, a 15.8 kb plasmid, contains a bacterial origin, G418-resistance gene, and yeast ARS, CEN and Tetrahymena TEL elements (GenBank Accession number No. U13189). Four mammalian origins have been cloned into this circular vector: 343, a 448 bp chromosomal origin from a transcribed region of human chromosome 6q (Shihab-El-Deen, A. et al. (1993) *Somat. Cell Mol. Genet.* 19:103–109); X24, a 4.3 kb element containing the hamster DHFR origin of bidirectional replication (oriβ)(Zannis-Hadjopoulos, M. et al. (1994) *Gene,* 151:273–277), and S3, a 1.1 kb human anti-cruciform purified autonomously replicating Nielsen, T. et al. (1994) *Mol. Gen. Genet.* 242:280–288) and A3/4, a version of the 36-bp consensus sequence. The resulting constructs (Y.343, Y.X24, YAC.S3, Y.A3/4, respectively) have been transfected into HeLa cells, and G418-resistant subcultures were isolated. The frequency of G418-resistant transformation was higher with origin-containing pYACneo than with vector alone. After >45 generations under G418 selection, the presence of episomal versus integrated constructs was assessed by fluctuation assay, and by PCR of supercoiled, circular and linear genomic cellular DNAs separated on EtBr-CsCl gradients. In stable G418-resistant subcultures which had been transfected with vector alone as well as in some subcultures transfected with circular origin-containing constructs, resistance was conferred by integration into the host genome. However, examples were found of G418-resistant transfectants maintaining the Y.343, YAC.S3 and Y.A3/4 circular constructs in a strictly episomal state after long-term culture in selective medium, with 70%–90% stability per cell division. Assays of some episomal constructs, as detected by PCR, found the constructs present in the supercoiled episomal and not the linear genomic CsCl fraction. These versatile constructs, containing mammalian origins, have the capacity for further modification with human telomere or large putative centromere elements, in an effort to move towards construction of a human artificial chromosome.

Materials and Methods

Molecular Cloning

The pYACneo (Clontech) vectors were digested with EcoRI. The 1.1 kb EcoRI insert of plasmid S3 (Nielsen, T. et al. (1994) *Mol. Gen. Genet.* 242:280–288) was ligated directly into the dephosphorylated vector, whereas the 448 bp EcoRI/HincII insert of pURHc34 (Wu, C. et al. (1993a) *Biochim. Biophys. Acta,* 1174:241–257) and the 4.3 kb XbaI fragment of pX24 (Burhans, W. C. et al. (1990) *Cell,* 62:955–965) were blunt-ended with T4 DNA polymerase before ligation into blunt-ended, dephosphorylated vector. A3/4, a version of the 36-bp consensus sequence contained in a 229 bp DNA fragment with suitable multicloning sites (e.g. NotI) and T3 primer and M13 reverse primer sequences, was ligated into EcoRI-digested, dephosphorylated pYAC-neo vectors. The resulting circular constructs are designated YAC.S3, Y.343, Y.X24 and Y.A3/4. Each was used to transform competent *E. coli*, and ampicillin-resistant colonies were grown for large scale plasmid preparation. The structures of the cloned constructs were then confirmed by restriction enzyme digestion.

Transfection and Culturing Human Cells

HeLa cells, passaged once since resurrection from frozen stocks, were seeded in T-25 flasks at $1\times10^4/cm^2$, and grown for two days (in (α-MEM+10% FCS) before transfection with 20 μg pYACneo, YAC.S3, Y.343, Y.X24 or Y.A3/4 DNA by calcium phosphate coprecipitation. Two days post-transfection, cells were switched into medium containing 400 μg/mL G418, and a further two days later, T-25 flasks were trypsinized, counted, and $1\times10^5$ cells were seeded onto 60 mm dishes. The HeLa cells were cultured in G418 until 20 days post-transfection, when dishes were scored for visible growing drug-resistant colonies. Individual colonies were picked directly from the 60 mm dishes to isolate clonal subpopulations for further analysis. Cultures were maintained in 400 μg/mL G418 during this period, and had been actively growing for an estimated minimum of 45 doublings between the initial transfection and the subsequent analysis of the episomal versus integrated state of the transfected constructs.

Fluctuation Assay

For each cloned transfectant cell line to be tested, cells which had been maintained in G418 were counted and $4\times10^5$ cells were plated into two T-80 flasks, one containing drug-free nonselective medium, and one used for maintaining the culture in G418-selective medium. In parallel, cells were seeded at a similar density onto two 24-well plates (200 mm²/well), to allow their growth curves to be followed both in the presence and absence of drug selection. Triplicate wells were trypsinized and counted daily with a Coulter Counter ZM™ apparatus. After six days of growth, both T-80 flasks were trypsinized, counted, and diluted with either G418-containing or nonselective medium to final concentrations of 5 cells/mL. 200 μL aliquots were then distributed to each well of a 96 well plate (32 mm²/well). (Two plates were used for the case of cells which had been passaged in nonselective medium and were now being returned to G418). Eight days later, the number of wells containing a growing cell colony was scored under the microscope.

Demonstration of Episomal DNA

As a positive control, HeLa cells were transiently transfected with Y.X24, by calcium phosphate coprecipitation, and harvested 48 h later. Using standard methods, total DNA from approximately $5\times10^6$ cells was isolated from untransfected HeLa (negative control), transiently transfected HeLa, and the cloned transfectant cell lines to be tested. DNA preparations where mixed with 1 mg ethidium bromide and 75 µg of a carrier plasmid, in this case F9, a pBluescript clone containing a 0.5 kb human genomic insert (Nielsen, T. et al. (1994) *Mol. Gen. Genet.* 242:280–288). CsCl solution was added to a final density of 1.56 g/mL before ultracentrifugation in a VTi80™ rotor, 20 h at 67,500 rpm. Using the intact and nicked carrier plasmid bands as a visible guide to the position of supercoiled (lower band) and linear and relaxed circular (upper band) DNA, the two completely-resolved fractions were carefully removed by side puncture. Ethidium bromide was removed by two washes with CsCl-saturated isopropanol, and CsCl was removed by ethanol precipitation with two 70% ethanol washing steps.

Aliquots representing one-eighth of the purified DNA were used as template in two separate 50 µL PCR reactions. To amplify a 131 bp region of the neo gene present in the transfected constructs, but not in the native HeLa genomic DNA, primers 5'-TCA GGA CAT AGC GTT GGC T-3' (SEQ ID NO:6) and 5'-CGT CAA GAA GGC GAT AGA A-3' (SEQ ID NO:7), located in the neo gene, were used (at 0.4 µM) with a mixture of all four dNTP's (each at 0.2 mM), 1×Taq buffer, and 1 U Taq polymerase (Pharmacia). 28 cycles were performed, each 94° C., 20 sec denaturation; 50° C., 90 sec annealing; and 72° C., 30 sec extension; the first denaturation and the final extension steps were carried out for 5 min. To amplify a 423 bp unique region on the long arm of human chromosome 6, primers 5'-TGT GTA TGG GAC GGT AGT CA-3' (SEQ ID NO:8) and 5'-GGA GCA AGG CAG AAC TAC TC-3' (SEQ ID NO:9) (Wu, C. et al. (1993b) *Biochim. Biophys. Acta,* 1174:258–266) were used at 0.25 µM, with 1.5 U Taq, for 33 cycles (each 94° C., 60 sec; 50° C., 60 sec; 72° C., 60 sec) followed by a 5 min final extension. Products of both reactions were electrophoresed in a 1.6% agarose, 1×TBE (0.089 M Tris, 0.089 M Boric acid, 0.002 M EDTA, pH 8.0) gel.

Results

Cloning Mammalian Origins into a YAC Vector pYACneo is a versatile plasmid shuttle vector (Traver, C. N. et al. (1989) *Proc. Nat. Acad. Sci. USA* 86:5898–5902). Because it includes the prokaryotic ColE1 origin and an ampicillin resistance marker from pBR322, pYACneo can be grown in *E. coli* as a circular plasmid. Since this vector also contains the *S. cerevisiae* ARS1 replication origin and CEN4 centromere elements, it can alternatively be maintained as a circular yeast artificial chromosome, carrying the TRP1, URA3, and HIS3 selectable markers. In addition, pYACneo carries a gene conferring resistance to the drug G418, a trait which is selectable in mammalian cells. Thus, this vector can replicate in both *E. coli* and *S. cerevisiae*, and contains markers for the selection of stable bacterial, yeast, or mammalian cell transfectants.

Three mammalian sequences and a version of the 36-bp consensus sequence, A3/4, previously shown to permit autonomous replication in human cells have been cloned into pYACneo vectors at the EcoRI site (FIG. 1).

In the vector, prokaryotic sequences are indicated by a thin gray line. Functional yeast cis-acting chromosomal components are shown as open boxes, while yeast marker genes are indicated by shaded boxes contained within the circular vector. The mammalian-selectable G418 resistance marker is in black. Two human (343, S3), one hamster (X24) and a version of the 36-bp consensus sequence (A3/4) contained within a total of 229 bp DNA, as origin-containing, autonomously replicating sequences were cloned into pYACneo vectors at the EcoRI site; restriction sites indicating the orientation of the inserts are presented. In the pYAC-neo constructs containing X24, 343, and S3, restriction mapping indicated an approximately 220 bp deletion in the region of one of the TEL elements. The pYAC-neo construct containing the A3/4 consensus sequence appears intact, with no deletions detected in the pYAC-neo vector.

343 is a 0.45 kb cDNA clone derived from a transcribed region on the long arm of human chromosome 6 (Shihab-El-Deen, A. et al. (1993) *Somat. Cell Mol. Genet.* 19:103–109), to which in vivo origin activity has been localized by nascent strand PCR mapping (Wu, C. et al. (1993b) *Biochim. Biophys. Acta,* 1174:258–266). S3 is a 1.1 kb human sequence isolated by anti-cruciform immunoaffinity purification of genoluic DNA, followed by competitive selection for clones possessing strong autonomous replication activity by mass transfection and in vitro replication assays (Nielsen, T. et al. (1994) *Mol. Gen. Genet.* 242:280–288). X24 carries a 4.3 kb XbaI fragment from the hamster DHFR 3' region, and includes the predominant initiation site oriβ, as indicated by multiple techniques (Burhans, W. C. et al. (1990) *Cell,* 62:955–965; Zannis-Hadjopoulos, M. et al. (1994) *Gene,* 151:273–277). Finally, A3/4 is a 36-bp consensus sequence derived by sequence comparison of several mammalian ARS.

HeLa Transfection Efficiency is Higher With Origin-containing Constructs

Since the Y.343, YAC.S3, Y.X24, and Y.A3/4 constructs remain relatively small in size (all less than 21 kb), they can be grown in bacteria, and pure preparations can be transfected by the relatively high-efficiency calcium-phosphate coprecipitation method, unlike YACs in the 0.1–1.0 Mb range, which necessitate the use of techniques such as yeast spheroplast fusion for transfecting mammalian cells. Calcium phosphate-treated, mock-transfected cells resulted in no G418-resistant colonies; pYACneo vector devoid of any mammalian origin gave 45 colonies per $10^5$ cells plated. Importantly, the test constructs YAC.S3, Y.343, Y.X24, and Y.A3/4 gave 70–900% more stably transfected G418-resistant colonies than the vector alone, suggesting that the presence of a short, cloned origin-containing insert may facilitate the maintenance of the transfected neo trait in human cells.

Isolated colonies were cloned and grown in G418 to select for maintenance of the transfected constructs, and spent a minimum of 67 days (and in some cases up to 96 days) in culture before testing for the presence and stability of episomal neo-containing DNA.

Stability of Transfected Constructs

A protocol based on the Luria-Delbruck fluctuation assay permits calculation of the stability of the drug resistance marker during cell growth in non-selective medium. Stable transformants obtained in the usual fashion, through integration of the transfected marker into the host genome, maintain the drug resistance trait even in the absence of selective pressure. However, episomally-replicating DNA which lacks a functional centromere will not partition accurately at mitosis and will display a characteristic loss rate per generation.

Figure 2B:
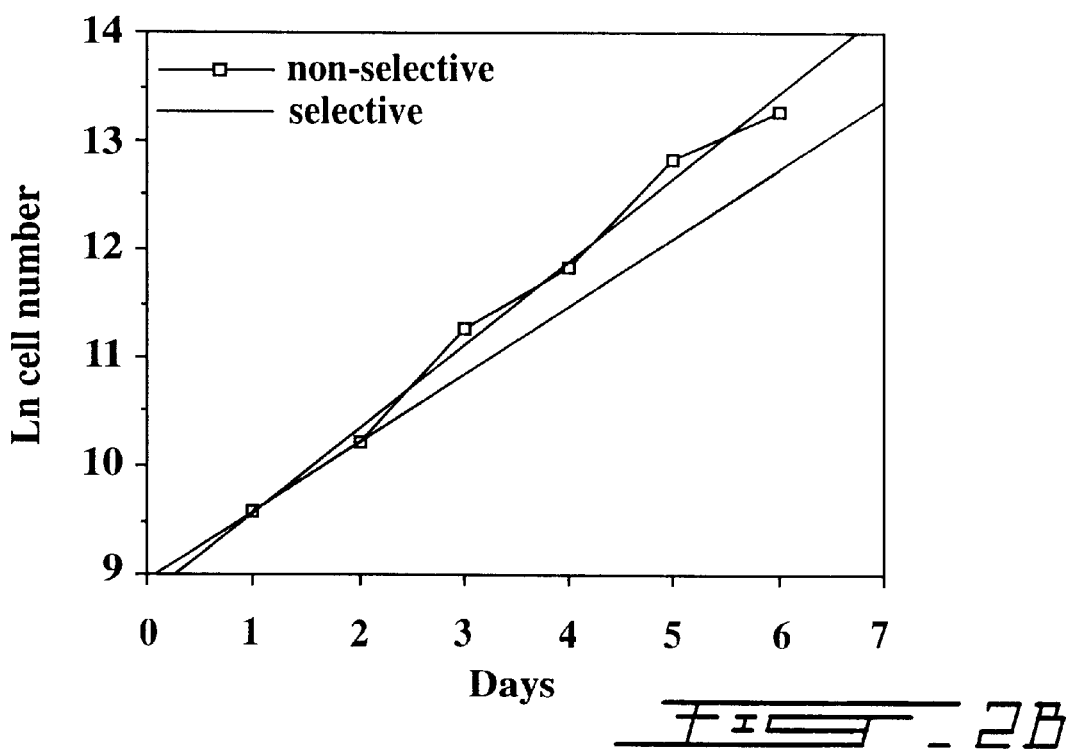

Examples of G418-resistant clonal cell populations initially transfected with circular pYACneo, YAC.S3, Y.343, or Y.X24, were tested by fluctuation assay. In essence, cells were passaged from G418 into nonselective medium and allowed to grow, while in parallel, cells were also seeded onto 24 well plates to allow daily monitoring of their growth rate. Examples of growth rates of individual clones are presented in FIG. 2.

After plating Y.343 clone 2 and Y.A3/4 clone 9 in 200 mm² wells, cell number was determined by Coulter count; each plotted point represents the average of triplicate wells for each day during log-phase growth. Open squares denote natural logarithm of the cell number in nonselective medium, while filled diamonds track growth in the presence of 400 μg/mL G418. For Y.A3/4 clone 9, the growth in selective medium was estimated from growth over 6 days (2 measurement points, at the beginning and 6 days after Some of the tested cell lines (including among others, YAC.S3 clone 1, Y.343 clone 2 and Y.A3/4 clone 9) grew slightly more slowly in G418 than they did in nonselective medium. (For example, see FIG. 2). A reduced population growth rate in G418 may reflect the loss of the neo marker during some cell divisions, or could instead reflect poor transcription of the neo gene in particular integrated contexts. From a regression analysis of these exponential growth curves in nonselective medium, the number of doublings which took place during the fluctuation period was calculated.

TABLE 1

In vivo stability of transfected constructs by fluctuation assay

| Host Cell | Transfection | # growing colonies on 96 well plates after fluctuation | | number of generations | STABILITY |
| --- | --- | --- | --- | --- | --- |
| | | G418[a] | non-selective[b] | #gen[c] | per division[d] |
| HeLa | YACneo clone 1 | 57 | 44 | 3.2 | 1.0 |
| HeLa | YACneo clone 2 | 42 | 47 | 2.8 | 0.9 |
| HeLa | YACneo clone 3 | 58 | 69 | 2.8 | 0.9 |
| HeLa | YAC.S3 clone 1 | 36 | 64 | 2.9 | 0.8 |
| HeLa | YAC.S3 clone 2 | 26 | 28 | 3.0 | 1.0 |
| HeLa | Y.343 clone 1 | 20 | 14 | 3.2 | 1.0 |
| HeLa | Y.343 clone 2 | 26 | 56 | 3.4 | 0.8 |
| HeLa | Y.343 clone 11 | 23 | 38 | 3.8 | 0.9 |
| HeLa | Y.343 clone 20 | 28 | 59 | 6.3 | 0.9 |
| HeLa | Y.X24 clone 1 | 18 | 28 | 3.5 | 0.9 |
| HeLa | Y.A3/4 clone 9 | 62 | 79 | 6.8 | 0.9 |
| S. cerevisiae | circular ARS plasmid | | | | 0.7[e] |
| S. cerevisiae | linear ARS plasmid | | | | 0.8[e] |
| S. cerevisiae | CEN-containing YAC | | | | 0.9–0.999[e] |
| S. pombe | circular ars plasmid | | | | 0.7[e] |
| S. pombe | cen-containing YAC | | | | 0.98–0.999[e] |
| Any host cell | integrated DNA | | | | 1.0 |

[a]G418 = number of wells containing growing colonies, after test clone cells, grown in non-selective medium for six days, were returned to G418 selective medium while plating at one cell per well onto 96 well plates.
[b]nonselective = number of wells containing growing colonies, after test clone cells, grown in non-selective medium for six days, were kept in nonselective medium while plating at one cell per well onto 96 well plates.
[c]#gen = the number of cell divisions which took place during the six day nonselective fluctuation period, as assessed by daily counts of parallel cultures.
[d]STABILITY per division (x) refers to the chance, following each cell division, that a daughter cell will inherit the selectable marker, and is calculated from the following relation:
$x^g$ = % PE (selected with G418)/% PE (unselected) where, g = number of cell generations and % PE = percent plating efficiency = # of 96 wells with colonies/96. Results are shown to one significant figure, where 1.0 is the maximum stability possible.
[e]Data from Murray & Szostak (1983), and Hahnenberger et al. (1989). Stability of centromere-containing yeast artificial chromosomes increases as a function of size.

culture). Solid straight lines were derived by linear regression analysis, from which the population doubling time is determined; in all cases the curve fit correlation ($R^2$) value was better than 0.98.

Six days after seeding into nonselective medium, while the cells -were still in log phase, the test flasks were trypsinized, diluted, and replated to determine the proportion of cells that still retained the neo marker. Results are shown in Table 1, along with the calculated stability of the constructs in each of the subpopulations tested.

All HeLa clones carrying circular pYACneo vector maintained the neo marker with a stability of approximately 1, supporting the hypothesis that their transfection is the result of integration events. The same is true for several of the clones transfected with origin-containing constructs. However, for example, in one of two YAC.S3, one of two Y.343, and a Y.A3/4 HeLa cell clone(s), a significant proportion of the cells in each population lost the G418 resistance trait during the nonselective fluctuation period, strongly suggesting that these clonal lines carried only episomal forms of the transfected constructs. Indeed, their calculated stability of 0.8–0.9 per generation is similar to that obtained by others during construction of S. cerevisiae and *S. pombe* yeast artificial chromosomes, using equivalent plasmids which carried a functional origin but lacked a centromere (Table 1). This reduced stability predicts that the trait would be lost in long-term nonselective culture; thus, to confirm the result from the six day fluctuation assay, the ultimate instability of the episomally-maintained neo marker in Y.343 clone 2 was tested by repeating the fluctuation assay, this time using a 46-day period of nonselective growth, with no G418-resistant colonies detectable.

HeLa Cells Maintain Human Origin-containing YACs as Episomes

Initial attempts to differentiate episomal from integrated DNA by Southern blots of low and high molecular weight Hirt lysate fractions were hampered by a poor detection threshold, inadequate separation of 20-kilobase episomes from genomic DNA, and the inability, following restriction digests, to distinguish episomal DNA from the product of head-to-head multimeric integration events. Nevertheless, results suggested that in Y.343 clone 1, and in YACneo clones 1 and 2, transfected constructs were integrated into the genome, whereas Y.343 clone 2 carried intact Y.343 at a total copy number of approximately 30 per cell; other Southern analyses for copy number in YAC.S3 clone 1 were not sensitive enough to reliably detect significant copies/cell, and, therefore, the copy number was assumed to be much lower than in Y.343 clone 2. Southern analyses of low molecular weight Hirt lysate fractions from Y.A3/4 clone 9 HeLa cells, as well as other Y.A3/4 transfected HeLa cell clones, after approximately 45 cell generations indicated that Y.A3/4 episomes of approximately 16 kb had been maintained. Using an alkaline cell lysis technique (Sun, T. Q. et al. (1994) *Nature Genet.* 8:33–41), which selects for covalently closed circular DNA, we found that Y.343 is present in clone 2 at 119 days after transfection, but only in the case where G418 selection was constantly maintained. Consistent with the results of the fluctuation assay, no pYACneo sequence of Y.343 was detected in the Y.343 clone 2 cell population that had been passaged in non-selective medium between day 89 and lysis on day 119.

In an effort to confirm that the modified YAC plasmids containing human origins were indeed being maintained in episomal form, total DNA was isolated from HeLa subclones YAC.S3 clone 1 and Y.343 clone 2, which had demonstrated instability of the drug resistance marker during fluctuation assay. CsCl/ethidium bromide density gradient ultra-centrifugation was, in fact, originally developed as a means for separating episomal from genomic DNA in HeLa cells, and conveniently resolves covalently-closed circular DNA from linear DNA and nicked (form II) circular DNA, which intercalate more of the buoyant dye. Any unrelated plasmid preparation which has accumulated 50% nicked and linear forms can serve as a visible guide to the position of the lower (supercoiled episomal) and upper (predominantly linear genomic) bands in the density gradient. DNA fractions prepared in this fashion from the HeLa subclones, as well as from positive and negative controls, were analyzed by PCR, using primers from the neo gene (FIG. 3).

Total DNA from HeLa subcultures was fractionated by CsCl/EtBr ultracentrifugation, using a carrier plasmid as a guide to the position of the lower band (L) containing supercoiled circular DNA, and the upper band (U) containing linear and relaxed circular forms of DNA. Fractions were tested for the presence of the transfected constructs by PCR amplification using a primer pair directed against the neo marker and yielding a 131 bp product (positive control template is a pure Y.X24 plasmid sample). The position of linear genomic chromosomal DNA was confirmed in a separate amplification, shown in the three rightmost lanes, using primers that recognize a unique region (423 bp) on human chromosome 6 (positive control is total genomic DNA isolated from the ME180 human cell line, ATCC HTB 33).

DNA from normal, untransfected HeLa cells did not yield a PCR product (only the carrier plasmid is visible) since these cells do not carry a neo gene. A polyclonal population of HeLa cells, transfected with Y.X24 48 h before DNA preparation, contained large quantities of PCR template in both the lower (intact circular) and upper (nicked or damaged circular, or integrated) CsCl gradient bands. However, the test clones yielded a product from only the lower, episomal DNA fraction, indicating that the transfected YAC.S3 and Y.343 constructs are being maintained, in these subcultures, as covalently closed circular episomes during long-term culture in selective medium (81 days for YAC.S3 clone 1; 96 days for Y.343 clone 2). The rightmost lanes show, through the use of primers directed at a unique genomic locus, that the linear genomic DNA segregates exclusively to the upper CsCl band. The lower band is free from contaminating genomic DNA. There appears to be no integrated copies, since the neo marker was not detected in the upper band fraction of DNA from those clones.

Control of Semiconservative Replication By Origin Consensus Sequence

HeLa cells were transfected with alphaconsensus clones and a uniorsconsensus clone as previously described (Wu, C. et al. (1993a) *Biochim. Biophys. Acta,* 1174:241–257), and then cells growing in log phase were pulsed with 40 µM bromodeoxyuridine for 48 hours before harvesting low molecular weight DNA by Hirt's extraction, and loading onto a neutral cesium chloride gradient. Approximately 200 µl fractions were collected, with fraction 1 representing the bottom of the gradient (abscissa). Refractive indices were measured using a refractometer (ordinate, Y2 axis), and samples from each fraction were loaded onto a dot blot manifold and hybridized with pYACneo probe. The total amount of DNA as quantified by Phosphoimage analysis is shown by the solid black bars (ordinate, Y1 axis).

FIG. 5 demonstrates examples of the control of semiconservative DNA replication by alphaconsensus sequences and a uniorsconsensus sequence when placed in a plasmid, e.g. pCRscript. FIG. 5A is pCRscript containing alphaconsensus A3/4: CCTCAAATGGTCTCCAATTTTCCTTTG-GCAAATTCC (SEQ ID NO:10); FIG. 5B is pCRscript containing alphaconsensus A16: CCTCGATGGGTTTG-CAAATTCCCCTTAGCAAATTCC (SEQ ID NO:11); FIG. 5C is pCRscript containing uniorsconsensus U22: ATATAAATGATAAAGTAAAATGAGGAT-TAAATAAGGACCTTTAATTAGGGTTTA-GATAGGGGATTTATAACGATATTATTTATAGCAGTTT (SEQ ID NO:12).

Both single- and double-strand substitution of bromodeoxyuridine are present in all cases. A3/4, FIG. 5A is particularly potent at controlling DNA replication in HeLa cells. Another version of the alphaconsensus, A16, FIG. 5B also acts a potent origin of DNA replication. In FIG. 5C, a lower but highly significant amount of DNA replication is controlled by the presence of a version of the uniorsconsensus sequence U22, acting as an origin of DNA replication.

Y.343 DNA Clone Which has 70% Homology With Alpha Consensus

Figures 6A, 6B:
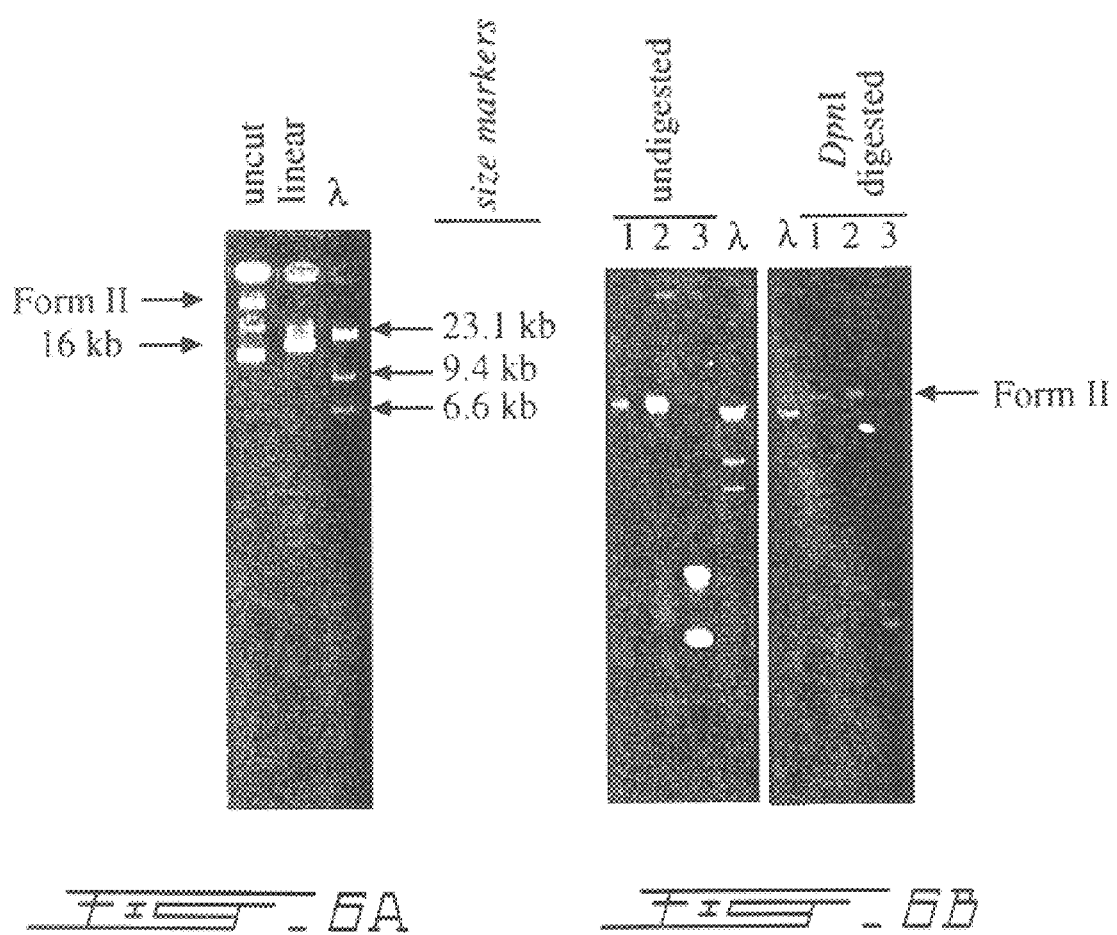
FIGS. 6A–6B illustrate the isolation of episomal DNA from stable HeLa cell clones.

For agarose gel electrophoresis of Y.343 input DNA used to transfect HeLa cells, uncut represents uncut Y.343 plasmid DNA (FIG. 6A). The positions of migration of different forms of DNA are indicated at the left hand side with arrows. Linear represents Y.343 plasmid DNA which has been linearized by digestion with SalI; λ represents molecular weight markers, the sizes of which are indicated at the right hand side with arrows (FIG. 6A).

Isolation and DpnI digestion of low molecular weight DNA from stable HeLa cell clones approximately 45 cell generations after transfection with Y.343. Low molecular weight DNA was extracted using Hirt's extraction method. 1 represents DNA from stable HeLa cell Y.343 clone 11; 2 represents DNA from stable HeLa cell Y.343 clone 20; 3 represents pBluescript DNA (500 ng). The second panel represents the same DNAs, but digested with 1 unit of DpnI for 1 hour at 37° C. (FIG. 6B).

FIG. 6 illustrates the nature of Y.343 DNA as recovered from HeLa cells after 45 cell generations. In lane 1 of Panel B is DNA obtained from HeLa cells of the Y.343 clone 11, and lane 2 is DNA obtained from HeLa cells of the Y.343 clone 20. In lane 3 is 500 ng of pBluescript DNA for control of DpnI digestion. In both clones, the majority of DNA is in recovered as form II, relaxed circular, and it is resistant to extensive DpnI digestion. (Note complete disappearance of pBluescript DNA with only some small digestion products visible.) The Y.343 DNA can be recovered from these HeLa cell clones after extensive replication during at least 45 cell generations.

Figure 7A:
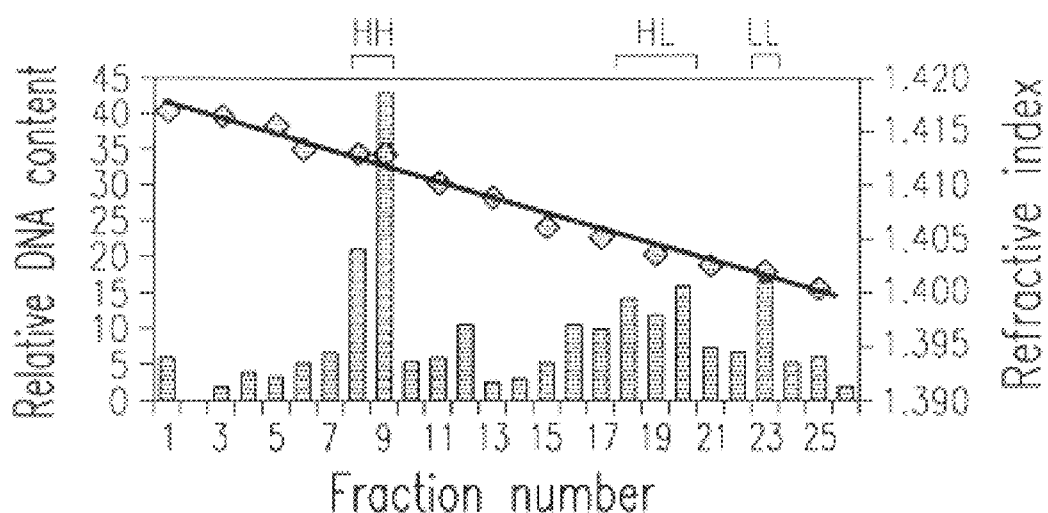
FIGS. 7A–7B illustrate bromodeoxyuridine in vivo labeling and recovery of episomal DNA from stable HeLa cell clones.

For the bromodeoxyuridine incorporation into nascent DNA, cells growing in log phase were pulsed with 40 $\mu$M bromodeoxyuridine for 48 hours before harvesting low molecular weight DNA by Hirt's extraction, and loading onto a neutral cesium chloride gradient (FIG. 7A). Approximately 200 $\mu$l fractions were collected, with fraction 1 representing the bottom of the gradient (abscissa). Refractive indices were measured using a refractometer (ordinate, Y2 axis), and samples from each fraction were loaded onto a dot blot manifold and hybridized with pYACneo probe. The total amount of DNA as quantified by Phosphoimage analysis is shown by the solid black bars (ordinate, Y1 axis). The relative positions of heavy-heavy (HH, both strands substituted with bromodeoxyuridine), heavy-line (HL, a single strand substituted with bromodeoxyuridine), and unsubstituted input light-light (LL) DNA are indicated. The signal obtained from dot blot analysis is indicated in the panel below the graph (FIG. 7A).

Figure 7B:
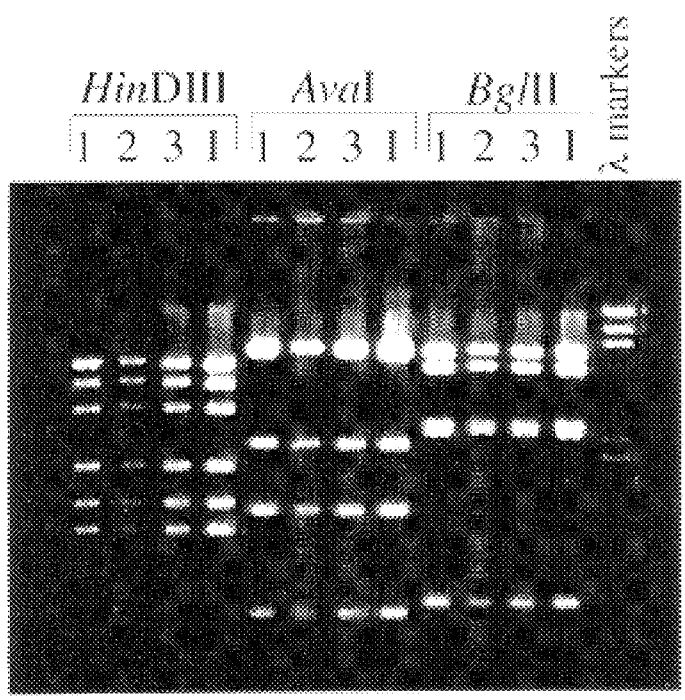

An ethidium bromide stained gel of plasmid DNA was obtained from bacteria transformed with episomal DNA isolated from stably transfected HeLa cell clone Y.343 clone 20, approximately 172 cell doublings after transfection (FIG. 7B). 'I' indicates the original input Y.343 plasmid DNA used to transfect the cells. Lanes 1–3 contain DNA from independent bacterial clones, digested with either HindIII, AvaI or BglII. Molecular weight sizes are indicated by the position of the markers in the far right lane (λ markers). Sizes are 23.1 kb, 9.4 kb, 6.6 kb, 4.4 kb, 2.3 kb, 2.0 kb and 0.6 kb.

FIG. 7 illustrates that the episomal DNA present in Y.343 clone 20 is semiconservatively replicated. Bromodeoxyuridine labeling of HeLa cell Y.343 clone 20 resulted in the recovery of single- and double-strand substituted Y.343 DNA after more than 170 cell generations after transfection. Restriction enzyme analysis of the Y.343 DNA, using three restriction enzyme did not indicate that there had been any significant rearrangements in three isolates (examples) of Y.343 DNA recovered from the HeLa cell Y.343 clone 20. The restriction fragment polymorphism was the same for each of the three isolates.

Specific Interaction Between OBA and the A3/4 DNA Consensus Sequence

The map and sequence characteristics of the 186 bp fragment of ors8 were previously reported (Todd, A. et al. (1995) *J. Cell. Biochem.* 58:221–236; Ruiz, M. T. et al. (1995) *J. Cell. Biochem.* 58:221–236).

In order to obtain the 186 bp fragment for band-shift experiments, ors8 plasmid was used as template in PCR reactions for amplification of the ors8 insert, which was then digested with NdeI and RsaI, as described previously (Todd, A. et al. (1995) *J. Cell. Biochem.* 58:221–236; Ruiz, M. T. et al. (1995) *J. Cell. Biochem.* 58:221–236). A nonspecific competitor fragment, pBRfg (206 bp), was prepared by PCR amplification of pBR322 DNA, as previously described (Ruiz, M. T. et al. (1995) *J. Cell. Biochem.* 58:221–236). Oligonucleotides containing the A3/4 sequence (36 nucleotides in length; 5'-CCTCAAATGGTCTCCAATTTT CCTTTGGCAAATTCC-3' (SEQ ID NO:10)) and a nonspecific competitor derived from pBR322 (16 nucleotides in length; 5'-TTCCGAATACCGCAAG-3' (SEQ ID NO:13)) were synthesized (Sheldon Biotechnology Centre, McGill University, Montreal), further purified by denaturing polyacrylamide gel electrophoresis (PAGE) and annealed as described by Wall et al. (Wall et al. (1988) *Gene*, 2:1089–1100). 5' end-labeling of the 186 bp fragment and A3/4 double-stranded oligonucleotide were performed as previously described (Ruiz, M. T. et al. (1995) *J. Cell. Biochem.* 58:221–236).

Band-shift competition experiments were performed in order to localize the binding site of OBA in the 186 bp fragment (FIG. 8).

Ten band-shift reactions were performed with radioactively labeled A3/4 DNA (10 ng/reaction) and 3.75 mg/reaction of protein from pool I (Sephacryl™ S-300, activity pool of OBA separating at approximately 150–200 kDa, obtained after separation of pool E ; Ruiz, M. T. et al. (1995) *J. Cell. Biochem.* 58:221–236), using the conditions described above. As a control, similar reactions were carried out in the absence of DNA. The band-shifts were analyzed by electrophoresis in a native 4% polyacrylamide gel, and the wet gel was exposed for 5 h at 4° C. for autoradiography. The OBA-DNA complexes were then excised from the gel, the proteins and the DNA were eluted from the gel by Ofverstedt et al. (1994) *Biochim. Biophys. Acta*, 782:120–126) and then subjected to electrophoresis on 8% SDS- polyacrylamide gel under reducing conditions. The proteins were then transferred electrically to an Immobilon™-P membrane (Millipore, Bedford, Mass.) and subjected to South-western analysis. Briefly, the membrane was incubated overnight (14–16 h) in blocking solution (buffer S: 25 mM Hepes-KOH, pH 7.7, 25 mM NaCl, 5 mM $MgCl_2$, 1 mM DTT containing 5% skim milk and 0.05% NP-40). The next day the membrane was subjected to a process of denaturation-renaturation, as follows: it was incubated for 10 min in a denaturing solution of 6 M guanidine hydrochloride in buffer S, followed by 10 min incubations in 3 M, 1.5 M, 0.75 M, 0.375 M and 0.187 M guanidine hydrochloride, respectively, diluted in buffer S; it was then washed twice for 10 min with buffer S, and incubated for 2 h in blocking buffer, followed by 1 h incubation in buffer S+1% skim milk. The membrane was then incubated overnight in hybridization solution (20 mM Hepes, pH 7.7, 75 mM KCl, 0.1 mM EDTA, 2.5 mM $MgCl_2$, 1% skim milk, 0.05% NP-40) containing radioactively labeled A3/4 oligonucleotide (5.2 ng/ml, 2.6×106 cpm/ml) in the presence of poly dI-dC (50 mg/ml) and pBRfg DNA (454 ng/ml) as nonspecific competitors. Finally, the membrane was washed three times with hybridization solution and subsequently exposed for autoradiography. The entire procedure was carried out at 4° C. and the incubations were done on a rocking platform.

In contrast to the nonspecific competitor, pBRfg, which did not compete, the different subfragments of the 186 bp competed to different extents for OBA binding. The most efficient competitor was the 59 bp fragment, resulting from the digestion of the 186 bp with MsII and FokI (FIG. 8), which competed as efficiently as, or better than the 186 bp fragment itself. The 59 bp fragment contains sequence homologous (80%) to a DNA sequence (A3/4, 36 bp), also present with varying homology in several different ors (Kaufmann, G. et al. (1985) Mol. Cell. Biol., 5:721–727; Landry, S. & Zannis-Hadjopoulos, M. (1991) Biochim. Biophys. Acta, 1088:234–244; Rao et al. (1990) Gene, 87:233–242) and other human replication origins isolated in our laboratory (Bell, D. et al. (1991) Biochim. Biophys. Acta, 1089:299–308; Wu, C. et al. (1993a) Biochim. Biophys. Acta, 1174:241–257; Nielsen, T. et al. (1994) Mol. Gen. Genet. 242:280–288). The A3/4 sequence was tested as competitor for OBA binding to the 186 bp fragment in the band-shift assay, and it was able to compete at least as well as the 59 bp fragment for the binding of OBA (FIG. 8). Furthermore, the specificity of OBA binding to the A3/4 sequence was tested in a series of competition band-shift assays, using the A3/4 oligonucleotide as specific competitor, in increasing (50–2000X) molar fold amounts. Formation of the OBA-A3/4 complex decreased in the presence of 50-fold molar excess of cold A3/4 oligonucleotide competitor, and it was completely abolished at 500-fold molar excess of A3/4. In contrast, when similar competition reactions were carried out using the two single-stranded oligonucleotides of the A3/4 sequence as competitors, neither was able to compete the OBA-A3/4 complex. A circular double-stranded plasmid containing the A3/4 consensus sequence was able, on the other hand, to compete for the OBA binding.

Figure 8A:
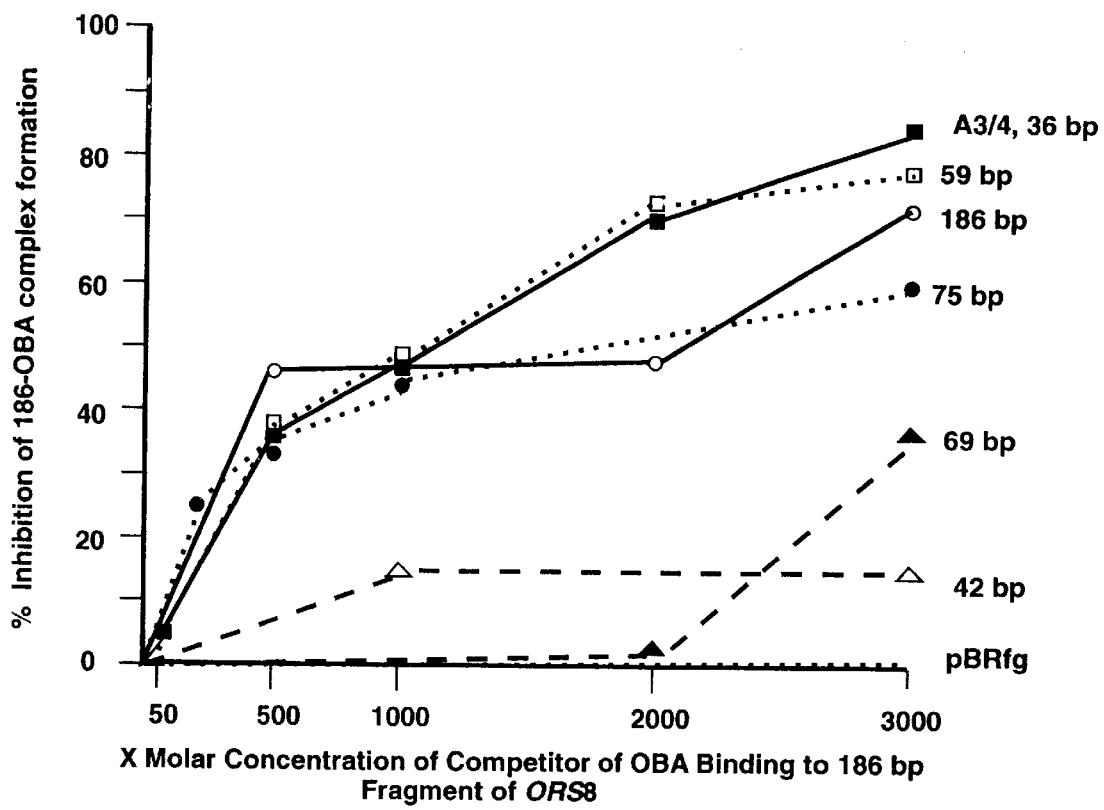
FIGS. 8A–8B illustrate a competition band-shift analysis of Ors Binding Activity protein binding.
Figure 8B:
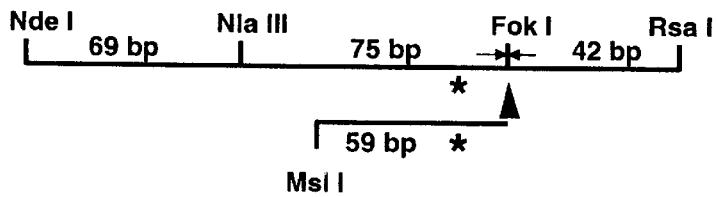

FIG. 8 illustrates the competition band-shift analysis of OBA binding. For FIG. 8A, band-shift reactions were performed, incubating constant amounts of both, protein (pool I; 200 ng) and radioactively labeled DNA (186 pb fragment; 0.1 ng). The various sub-fragments of the 186 bp sequence and the A3/4 (36 bp) sequence were used as cold competitors at the molar-fold excess level indicated. The shifted complexes were quantitated by densitometry and the results expressed as percent reduction in complex formation. In FIG. 8B, there is shown a restriction map of the 186 bp sequence of ors8 indicating the fragments used as competitors. The FokI site (arrow point) bisects the inverted repeat (><). The position of the A3/4 homologous sequence is indicated (*).

A3/4 Oligonucleotide Inhibits the in vitro DNA Replication of p186

To investigate the effect of the A3/4 sequence on the in vitro replication of p186, in vitro reactions were performed using increasing molar excess amounts of either the A3/4 oligonucleotide or a pBR322-derived nonspecific oligonucleotide as competitors.

In vitro replication was carried out as previously described (Pearson, C. E. et al. (1991) Biochim. Biophys. Acta 1090:156–166 Todd, A. et al. (1995) J. Cell. Biochem. 58:221–236), with slight modifications. In the experiments involving the addition of the A3/4 oligonucleotide, increasing molar excess amounts of either the A3/4 or pBR322 oligonucleotides were added relative to the p186 (200 ng) input template DNA. A pre-incubation of the HeLa cell extracts with the oligonucleotides for 20 min on ice preceded the in vitro replication reaction, carried out as previously described (Pearson, C. E. et al. (1991) Biochim. Biophys. Acta 1090:156–166; Zannis-Hadjopoulos, M. et al. (1994) Gene, 151:273–277; Todd, A. et al. (1995) J. Cell. Biochem. 58:221–236). The reaction products were divided into three aliquots: one third was digested with DpnI (1 U; New England BioLabs), as previously described (Pearson, C. E. et al. (1991) Biochim. Biophys. Acta, 1090:156–166 Todd, A. et al. (1995) J. Cell. Biochem. 58:221–236), and two thirds were kept undigested. The DpnI-digested and one third of the undigested products were subjected to electrophoresis on 1% agarose gel in 1× TAE buffer (16–20 h, 50–55 Volts). The gels were dried and exposed to DuPont reflection NEF-autoradiographic film. Quantification was performed on DpnI-digested products, as previously described (Todd, A. et al. (1995) J. Cell. Biochem. 58:221–236), by densitometric measurements using a Phosphoimager™ analyzer (Fuji BAS 2000) or a Bio Image Densitometer™ (MillGen/Biosearch); both methods gave similar results.

Figure 9:
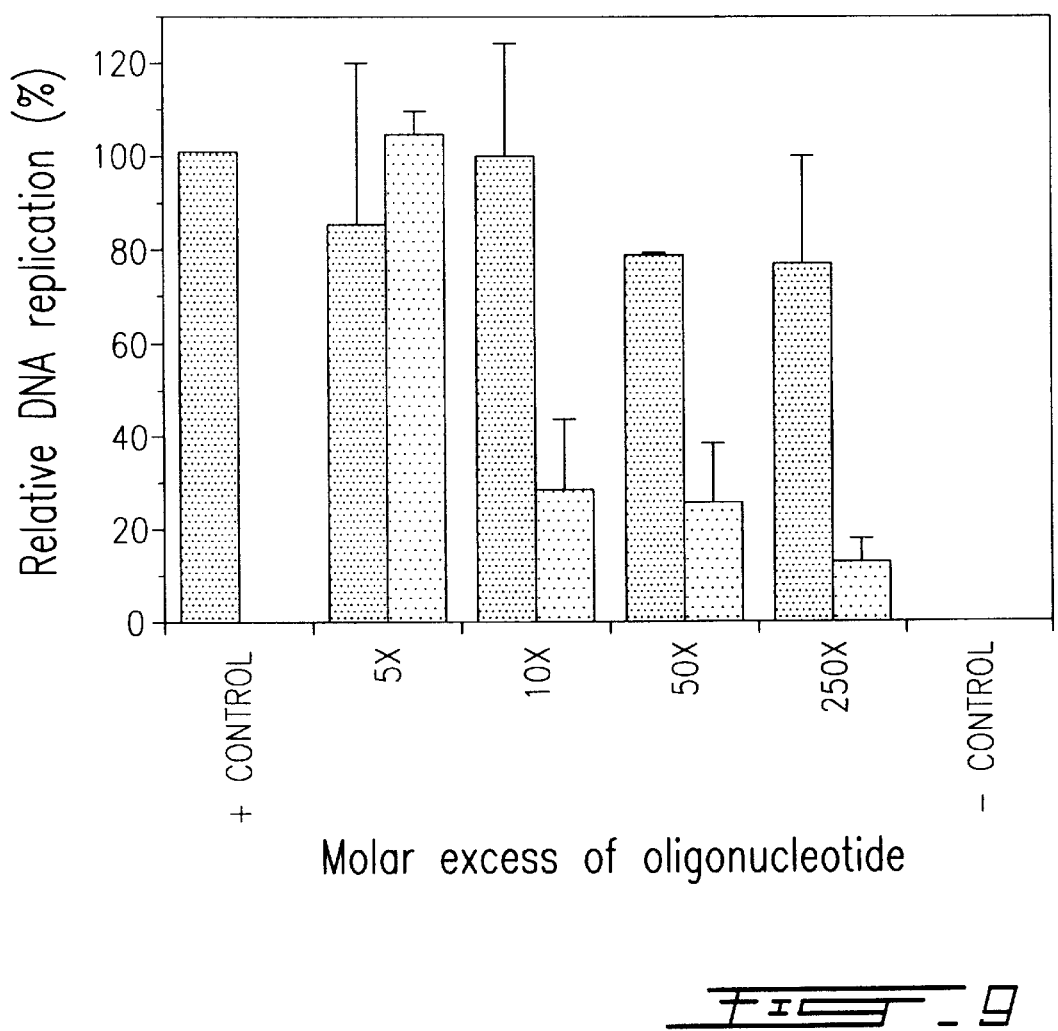
FIG. 9 illustrates the effect of the double-stranded A3/4 oligonucleotide sequence on the in vitro replication of p186.

While inclusion of the nonspecific oligonucleotide in the in vitro reaction did not affect the replication of p186, addition of increasing amounts of the A3/4 oligonucleotide strongly inhibited its replication in vitro, decreasing it by approximately 4-fold at 10× molar excess and by approximately 10-fold at 250× molar excess amounts to the p186 template (FIG. 9).

FIG. 9 show the effect of the A3/4 oligonucleotide sequence on the in vitro replication of p186. A. p186 plasmid (200 ng), containing the 186 bp fragment of ors8, was used as template for in vitro replication. Increasing molar excess amounts (indicated) of the A3/4 (gray bars) or pBR322 (black bars) oligonucleotides to p186 template were used as specific and non-specific competitors, respectively.

Discussion

Mammalian origin sequences have been cloned into a versatile shuttle vector, capable of further modification and of growth in several host systems. These constructs remain small enough to be transfected into human cells by calcium phosphate coprecipitation, and are selected for using the neo marker.

The efficiency of stable transfection is increased 1.7- to 10-times by the presence of an origin sequence, in line with previous observations using a cloned portion of the human 5' c-myc (McWhinney, C. & Leffak, M. (1990) Nucl. Acids Res. 18:1233–1242). Attempts have been made to use YAC vectors to transfect large genomic regions (hundreds of kb) into mammalian cells (Forget, 1993), but again stable transfection required integration into the host genome. Nonet & Wahl (Nonet, G. H. & Wahl, G. M. (1993) Somat. Cell Mol. Genet. 19:171–192) cloned a 70 kb region including the mouse 5' adenosine deaminase origin into a YAC and transfected mouse cells by yeast spheroplast fusion. In this case, examples were found of stable transfectants harboring episomally-replicating circular constructs, but only in the presence of coexisting integrated copies. Featherstone & Huxley (Featherstone, T. et al. (1993) Genomics, 17:267–278) used yeast sphero-plast fusion to transfect mouse cells with a 660 kb YAC carrying a large, selectable human genomic insert (presumed to carry several replication origins), and observed transfected subpopulations which maintained otherwise unstable episomes under long-term selection. However, these episomes were the result of extensive recombination among yeast, mouse and human DNA and could not be fully characterized; in cell lines in which transfected DNA existed strictly in episomal form, much of the human DNA had apparently been lost. The modified YACs used here to transfect human cells are completely defined, can be grown in bacteria or yeast, can be transfected by calcium phosphate coprecipitation (which gives higher transformation efficiencies and does not cotransfect yeast genomic DNA), and both YAC.S3, Y.343 and Y.A3/4 have been demonstrated to be capable, in a G418-selected human cell system, of persisting for several months in a purely episomal form.

However, cells which carry episomal neo grow more slowly in G418 than in nonselective medium, in contrast to cells in which integration has occurred, in which the growth in G418 is nearly identical to the growth in nonselective medium. This observation may help identify episomal cell lines, but it is not a specific test since a subset of integrated cell lines also exhibit slow growth in G418.

The copy number (estimated as 30) of Y.343 clone 2 is similar to that observed in yeast harboring circular ARS plasmids (Murray, A. W. & Szostak J. W. (1983) Nature, 305, 189–193). This apparent amplification results from inaccurate partition of plasmids at mitosis, and reaches an equilibrium in long-term culture above some threshold value needed for sufficiently stable maintenance and cell growth under selection. High copy numbers cannot confer a mitotic stability greater than 80–90%, which requires the presence of an element (such as a centromere) directing accurate partition.

The overall stability of YAC.S3, Y.343 and Y.A3/4 episome maintenance during growth in nonselective medium is comparable to that obtained with autonomously replicating yeast plasmids (Table 1), which constituted the first step in the construction of yeast artificial chromosomes. It is likely that very large domains of DNA, tens to hundreds of kilobases will contain their own replication origins. However, the delimitation of a minimal human centromere through minichromosome analysis would require and benefit from the presence, in cis, of a separate, defined replication origin. The constructs described here are sufficiently versatile to allow addition of cloned human telomeres and of large putative centromeric blocks with or without intrinsic replication origins; they can be manipulated as a small and easily-engineered bacterial plasmid, as a small or large circular or linear yeast artificial chromosome, or as an episomal genetic element in human cells which can be assayed for mitotic stability. Stability in nonselective medium would be expected to be enhanced, from about 80–90% to more than 99.99%, in larger constructs containing a centromere.

Vectors capable of long-term persistence in mammalian cells have been constructed by others, but these rely on viral origins of DNA replication. Examples include a murine plasmid based on a defective polyoma virus (Gassman, M. et al. (1995) Proc. Nat. Acad. Sci. USA, 92:1292–1296), and a "human artificial episomal chromosome" which carries the EBV latent origin, oriP (Sun, T. Q. et al. (1994) Nature Genet. 8:33–41). While capable of acting as excellent gene vectors in vitro, such constructs are not helpful for studying mammalian chromosomal origin biology, and require the presence of viral transactivating proteins for their replication. Attempts to create artificial chromosomes by deleting large blocks from native chromosomes still leave huge undefined regions. The potential of a mammalian artificial chromosome, not only as a gene vector, but also as a model for addressing questions about chromosomal biology, may be best reached through a "ground-up" assembly of the functional cis-acting components, origins, telomeres, and centromeres. Origins represent the logical first step.

The present invention will be more readily understood by referring to the following example which is given to illustrate the invention rather than to limit its scope.

EXAMPLE I
Some Major Points Regarding Consensus Sequences

Based upon the consensus sequences, a pool of oligonucleotides was synthesized. The sequences synthesized were:

```
AATTCCTGCAGCCCGGGGGATCCGCCCATTAACCCTCAC
TAAAGGGAACAAAAGCTGGGTACC-consensus sequences-
TGAGCTCCAATTCACTGGCCGTCGTTTTACGGGCTAGAG
CGGCCGCCACCGCGGTGGAGCTCCAGCTTTTGTTCC
CTTTAGTGAGGGTTAATTGCGCGCTTGGCGTAATCATGG
TCATAGCTGTTTCCGG                 (SEQ ID NO:14).
```

Then, the consensus sequences were amplified by PCR using T7 and M13 reverse primers; the amplified products were cloned into the SnfI site of pCRscript (pCR-Script Amp SK (+) obtained from Stratagene) for individual variant sequence analyses. The ligated pool was directly transfected into HeLa cells and after three days, the low molecular weight fraction of DNA was isolated and digested with DpnI enzyme to remove unreplicated plasmid vector+ consensus sequence inserts. The pool of variants subjected to DpnI digestion was then used to transform bacteria; undigested plasmid vector+consensus sequence insert DNA would have been replicated in human cells and thus contain consensus sequences essential to the initiation and control of DNA replication in mammalian cells. These functional assays were used to select the alphaconsensus and uniorsconsensus variants which were most efficient in allowing DNA replication in HeLa cells.

Both results indicated that variants of alphaconsensus and uniorsconsensus were effective in allowing DNA replication in mammalian cells of circular episomes.

DpnI resistance assays after transfection of individual clones into HeLa cells demonstrated that a sample of the recovered variants could be replicated by human cells.

DpnI resistance assays after replication in an in vitro mammalian DNA replication system, using extracts of HeLa cells (Pearson, C. E. et al. (1991) Biochim. Biophys. Acta 1090:156–166), also demonstrated replication of circular episomes by human replication proteins.

Using the in vitro replication system, initiation of DNA replication was shown to occur within the alphaconsensus sequence. (See FIG. 4).

A3/4 alphaconsensus was cloned into pCRscript at the snfI site. An earliest labeled fragment assay or preferential labeling assay for the A3/4 version of the alphaconsensus containing insert at early times of in vitro DNA replication was assessed at 4 and 8 minutes of reaction. The reaction mixture contained both $^{32}$p-labeled -dCTP and -dTTP to monitor DNA synthesis in the system. After extraction and purification of DNA, the products were digested with DdeI and PvuII before analysis by gel electrophoresis, radioautography and quantitative densitometry. The results were expressed in arbitrary units as relative incorporation per kilobase for each fragment.

An activity previously characterized as OBA (Ruiz, M. T. et al. (1995) J. Cell. Biochem. 58:221–236), binds competitively with sequence from a monkey sequence with origin activity.

One form of the consensus noted as A3/4 has been cloned into pYACneo, yeast artificial chromosome cloning vector (Genbank Accession No. U13189, obtained from Clontech), at the EcoRI site. The A3/4 version of the consensus is:

CCTCAAATGGTCTCCAATTTTCCTTTGGCAAATTCC (SEQ ID NO:10). The resultant clone was transfected into HeLa cells with an efficiency approximately 10 times greater than the pYACneo vector alone.

The Y.A3/4 containing HeLa cells were analyzed for stability of maintenance without G418 selection after 45 cell generations of selection. Changes in the population doubling time as affected by G418 selection, indicated that five out of seven clones had lengthened doubling times with selection The stability of maintenance of resistance to G418 selection for these clones was found to be between 0.8–0.9/cell/generation, suggesting the phenotype was maintained by extrachromosomal elements.

Southern blot analyses of low molecular weight DNA reveals the presence of episomal Y.A3/4 in cells after passage for 60–65 generations under selective pressure (G-418). Resistance to digestion with endonuclease DpnI indicates the episomes had been replicated in the mammalian cell host, HeLa cells. Incorporation of bromodeoxyuridine into Y.A3/4 episomes clones of HeLa cells transfected with Y.A3/4 indicates that Y.A3/4 is replicated semiconservatively.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated human or mammalian DNA replication origin sequence consisting essentially of a sequence selected from the group consisting of: SEQ ID NO:1, functional variants thereof having a sequence of at least 70% homology, and functional fragments thereof having at least 20 nucleotides, with the proviso that the isolated sequence does not comprise CCTCTAATGGCTTCCAAACAT-CACTTGGCAAATTCC (SEQ ID NO:15).

2. An isolated DNA sequence for the maintenance of circular plasmid constructs which replicate semiconservatively in proliferating mammalian cells, which DNA sequence comprises at least one sequence consisting of a DNA replication origin sequence according to claim 1.

\* \* \* \* \*

UNITED STATES PATENT AND TRADEMARK OFFICE
CERTIFICATE OF CORRECTION

PATENT NO.     : 6,410,722 B1                                               Page 1 of 1
DATED          : June 25, 2002
INVENTOR(S)    : Gerald B. Price et al.

It is certified that error appears in the above-identified patent and that said Letters Patent is hereby corrected as shown below:

<u>Title page,</u>
Item [54], Title should read
-- HUMAN AND MAMMALIAN DNA REPLICATION ORIGIN CONSENSUS SEQUENCES --

Signed and Sealed this

Twenty-fourth Day of June, 2003

JAMES E. ROGAN
*Director of the United States Patent and Trademark Office*